(12) United States Patent
Akinci et al.

(10) Patent No.: US 11,187,451 B2
(45) Date of Patent: Nov. 30, 2021

(54) REFRIGERATOR COMPRISING ODOR REMOVAL DEVICE

(71) Applicant: ARCELIK ANONIM SIRKETI, Istanbul (TR)

(72) Inventors: Irem Akinci, Istanbul (TR); Mehmet Ercan Kaymak, Istanbul (TR); Ferkan Gulbas, Istanbul (TR)

(73) Assignee: ARCELIK ANONIM SIRKETI, Istanbul (TR)

( * ) Notice: Subject to any disclaimer, the term of this patent is extended or adjusted under 35 U.S.C. 154(b) by 91 days.

(21) Appl. No.: 16/476,254

(22) PCT Filed: Jan. 25, 2018

(86) PCT No.: PCT/EP2018/051815
§ 371 (c)(1),
(2) Date: Jul. 5, 2019

(87) PCT Pub. No.: WO2018/141620
PCT Pub. Date: Aug. 9, 2018

(65) Prior Publication Data
US 2019/0353418 A1    Nov. 21, 2019

(30) Foreign Application Priority Data

Feb. 2, 2017    (TR) .................. TRA 2017/01552

(51) Int. Cl.
*F25D 17/04*  (2006.01)
*A61L 9/20*  (2006.01)
*F25D 29/00*  (2006.01)

(52) U.S. Cl.
CPC ........... *F25D 17/042* (2013.01); *A61L 9/205* (2013.01); *F25D 29/005* (2013.01); *F25D 2317/0417* (2013.01); *F25D 2700/02* (2013.01)

(58) Field of Classification Search
CPC .............. A61L 9/205; F25D 17/042; F25D 2317/0417; F25D 2700/02; F25D 29/005
See application file for complete search history.

(56) References Cited

U.S. PATENT DOCUMENTS 4,327,557 A  *  5/1982  Clarke .................. F25D 21/006
                                                            62/153
5,482,685 A  *  1/1996  Fujita ................... B01D 53/885
                                                            392/485

(Continued)

FOREIGN PATENT DOCUMENTS

DE    102013218270 A1    3/2015
JP        5918649 B2    5/2016

(Continued)

OTHER PUBLICATIONS

International search report and written opinion, dated Apr. 24, 2018, of International Application No. PCT/EP2018/051815; 9 pgs.

*Primary Examiner* — Henry T Crenshaw
(74) *Attorney, Agent, or Firm* — Kilpatrick Townsend & Stockton LLP

(57) ABSTRACT

The present invention relates to a refrigerator comprising on or more cooler or freezer compartments in which food products are placed, a door enabling access to the compartment, and an odor removal device enabling cleaning the air emanating from the food products to the environment in the compartment and forming odor comprising: an UV light source provided in a housing, a fan, a photocatalytic filter and a plurality of openings provided on the housing, enabling passing the air received from interior of the compartment and delivered into the compartment by the fan, and a control unit operating the odor removal device in subsequent on-off periods according to a predetermined algorithm.

5 Claims, 1 Drawing Sheet

(56) References Cited

U.S. PATENT DOCUMENTS

| | | | | |
|---|---|---|---|---|
| 5,501,844 | A | * | 3/1996 | Kasting, Jr. .............. A61L 9/015 |
| | | | | 422/186.15 |
| 5,933,702 | A | * | 8/1999 | Goswami .................. F24F 3/12 |
| | | | | 422/186.3 |
| 2003/0086831 | A1 | * | 5/2003 | Horton, III ............. C03C 25/42 |
| | | | | 422/120 |
| 2007/0266725 | A1 | * | 11/2007 | Anikhindi ................. A61L 9/16 |
| | | | | 62/317 |
| 2011/0181163 | A1 | * | 7/2011 | Han ........................ F25D 11/00 |
| | | | | 312/405 |
| 2013/0061754 | A1 | * | 3/2013 | Lev ........................... B03C 3/53 |
| | | | | 96/15 |
| 2014/0360213 | A1 | * | 12/2014 | Son .......................... A61L 2/10 |
| | | | | 62/177 |
| 2016/0334158 | A1 | * | 11/2016 | Joo ....................... F25D 25/021 |
| 2017/0191728 | A1 | * | 7/2017 | Seo ....................... F25D 17/042 |
| 2018/0272024 | A1 | * | 9/2018 | Seo ....................... A23L 3/3418 |

FOREIGN PATENT DOCUMENTS

| | | | |
|---|---|---|---|
| KR | 20170003283 A | 1/2017 | |
| WO | 2006126584 A1 | 11/2006 | |
| WO | 2014019440 A1 | 2/2014 | |

\* cited by examiner

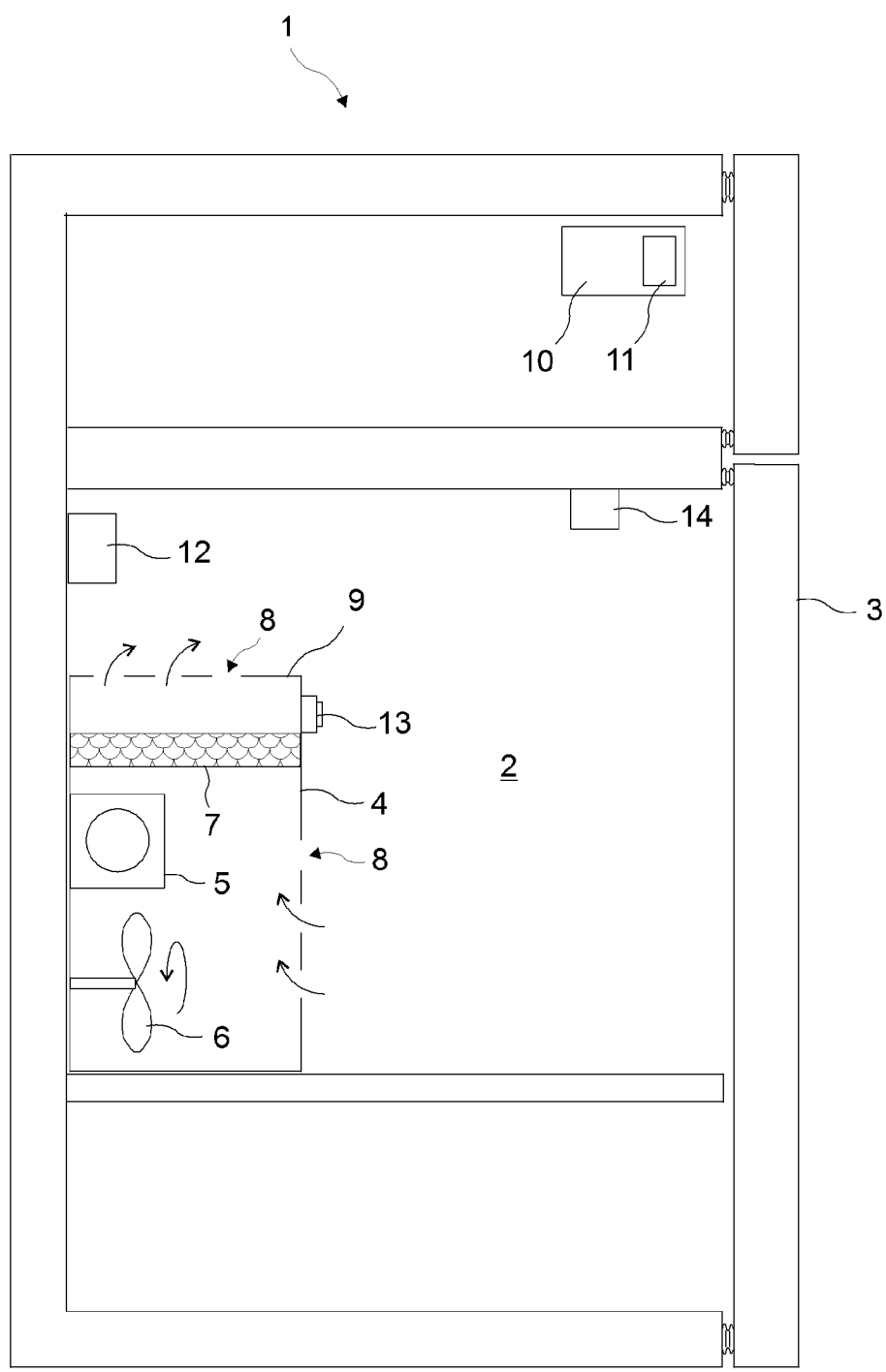

REFRIGERATOR COMPRISING ODOR REMOVAL DEVICE

RELATED APPLICATIONS

This application is a U.S. National Phase of International Application No. PCT/EP2018/051815, filed Jan. 25, 2018, claiming priority to Turkish Patent Application No. 2017/01552, filed Feb. 2, 2017, contents of which are hereby incorporated by reference in their entirety.

Research on user habits reveal that in some cases, food products are placed in refrigerators in open containers without any sealing, directly after their packages are opened or after being cooked, etc. This leads to odors being mixed in a refrigerator and formation of undesirable odors. In addition, undesirable odors form inevitably when food products stored in a refrigerator become spoiled. To remove the odors forming in a refrigerator, using odor removal devices including UV (ultraviolet) light source, is known. Together with photocatalytic filter, UV light source enables cleaning the air in a refrigerator, however, it is known that UV rays are harmful for users and measures should be taken for the UV lights not to affect a user.

International patent applications no. WO2014019440 and WO2006126584 disclose refrigerators in which odor removal devices are used.

The aim of the present invention is to realize a refrigerator comprising an odor removal device, wherein a user is avoided from being affected from rays radiating from a UV light source provided in said device.

In the refrigerator realized to achieve the aim of the present invention, an odor removal device is used enabling cleaning the air emanating from food products and forming odor, comprising an UV light source, a fan and a photocatalytic filter.

A control unit operates said odor removal device in subsequent on-off periods according to a predetermined algorithm. In the embodiment of the invention, upon detecting the door being open by means of detecting means such as "reed switch", or "hall effect sensor", the control unit disables the odor removal device by turning the UV light source off. Thus, the UV rays radiating from the UV light source and permeating from the gaps on the odor removal device, is prevented from affecting the user.

The refrigerator realized to achieve the aims of the present invention is illustrated in the accompanying drawings, wherein:

FIG. 1 is a schematic view of the refrigerator of the invention.

The elements in the figures are numbered individually and the correspondence of these numbers are given hereinafter.
1. Refrigerator
2. Compartment
3. Door
4. Housing
5. UV light source
6. Fan
7. Photocatalytic filter
8. Opening
9. Odor removal device
10. Control unit
11. Timer
12. Gas sensor
13. On-off button
14. Detecting means The refrigerator (1) comprises one or more cooler or freezer compartments (2) in which food products are placed, a door (3) enabling access to the compartment (2), and an odor removal device (9) enabling cleaning the air emanating from the food products to the environment in the compartment (2) and forming odor, comprising: an UV (ultraviolet) light source (5) provided in a housing (4), a fan (6), a photocatalytic filter (7) and a plurality of openings (8) provided on the housing (4), enabling circulating the air received from interior of the compartment (2) and delivered into the compartment (2) by the fan (6).

The refrigerator (1) of the invention comprises a control unit (10) operating the odor removal device (9) in subsequent on-off periods according to a predetermined algorithm, detecting whether the door (3) is open or closed by means of detecting means (14) such as "reed switch", or "hall effect sensor", and disabling the odor removal device (9) upon opening of the door (3) by turning the UV light source (5) and the fan (6) off if the odor removal device (9) is in operational period. If the odor removal device (9) is in inactive period when the door (3) is opened, then the control unit (10) delays operation of the odor removal device (9) until the door (3) is closed.

In the refrigerator (1) of the invention, the odor removal device (9) is disabled when the user opens the door (3), the UV light source (5) and the fan (6) are turned off, and the user is prevented from being subject to UV lights permeating from the openings (8) provided on the housing (4).

The refrigerator (1) further comprises a timer (11) detecting the durations in which the door (3) is open and the on-off periods of the odor removal device (9), and the control unit (10) regulates the operation of the odor removal device (9) according to data received from the timer (11).

In case the door (3) is opened by the user, the duration in which the door (3) is open is measured by the timer (11) and relevant data is transmitted to the control unit (10), and the control unit (10) enables including the duration in which the door (3) is open to the operational period of the odor removal device (9). The continuous operational period between disablements of the odor removal device (9) is determined to be 120 minutes.

In an embodiment of the invention, the refrigerator (1) comprises a gas sensor (12) detecting chemicals emanating from food products to the environment in the compartment (2) and forming odor. The control unit (10) assesses the signals transmitted by the gas sensor (12), and starts the operation of the odor removal device (9) if the detected odor amount is higher than a predetermined limit value. After activating the odor removal device (9), the control unit (10) continues operating it according to said algorithm. The odor removal device (9) is disabled upon opening of the door (3) and its operation is resumed upon closing of the door (3).

In another embodiment of the invention the refrigerator (1) comprises an of-off button (13) enabling the operation of the odor removal device (9) to be turned on or off "manually" by the user. The user can start the operation of the odor removal device (9) by means of the on-off button (13). After the odor removal device (9) being manually activated, the control unit (10) continues operating it according to said algorithm. The odor removal device (9) is disabled upon opening of the door (3) and its operation is resumed upon closing of the door (3).

In the refrigerator (1) of the invention, the user is prevented from being subject to UV lights by the odor removal device (9) being disabled by the control unit (10) upon opening of the door (3). The user can manually control operation of the odor removal device (9) by means of the on-off button (13).

The invention claimed is:

1. A refrigerator comprising:
    at least one compartment in which food products are placed,
    a door enabling access to the compartment, and
    an odor removal device enabling cleaning the air emanating from the food products to the environment in the compartment and forming an odor, wherein the odor removal device comprises:
        an UV (ultraviolet) light source provided in a housing,
        a fan provided upstream from the UV light source,
        a photocatalytic filter provided downstream from the UV light source, and
        a plurality of openings provided on the housing, enabling circulating the air received from an interior of the compartment and delivered into the compartment by the fan, wherein the fan faces the plurality of openings and draws the air from the interior of the compartment,
    a controller positioned outside of the compartment and configured to operate the odor removal device in subsequent on-off periods, detect whether the door is open or closed, and disable the odor removal device upon opening of the door by turning the UV light source and the fan off.

2. The refrigerator according to claim 1, further comprising:
    a timer detecting durations in which the door is open and the on-off periods of the odor removal device, wherein the controller is further configured to receive data from the timer, and regulate operation of the odor removal device according to the data received from the timer.

3. The refrigerator according to claim 1, further comprising:
    a timer detecting a duration in which the door is open, wherein the controller is further configured to include the duration in which the door is open to an operational period of the odor removal device.

4. The refrigerator according to claim 1, further comprising:
    a gas sensor detecting chemicals emanating from the food products to the environment in the compartment and forming the odor, wherein the controller is further configured to receive signals transmitted by the gas sensor, assess the signals transmitted by the gas sensor, and start the operation of the odor removal device if the detected odor amount is higher than a predetermined limit value.

5. The refrigerator according to claim 1, further comprising:
    an on-off button enabling the operation of the odor removal device to be turned on or off by a user.

* * * * *